United States Patent [19]

Shen et al.

[11] 4,205,400
[45] Jun. 3, 1980

[54] METALLO-POLYMERIC PROSTHESIS WITH CAVITIED INTERCONNECTION

[75] Inventors: George Shen, Winona Lake; Clayton R. Miller, Bremen, both of Ind.

[73] Assignee: Zimmer USA, Inc., Warsaw, Ind.

[21] Appl. No.: 965,850

[22] Filed: Dec. 4, 1978

[51] Int. Cl.² .............................................. A61F 1/24
[52] U.S. Cl. ...................... 3/1.91; 3/1.911; 128/92 C
[58] Field of Search ................... 3/1.9–1.913; 128/92 C, 92 CA

[56] References Cited

U.S. PATENT DOCUMENTS

| 2,668,531 | 2/1954 | Haboush | 3/1.912 |
| 3,813,700 | 6/1974 | Tavernett et al. | 3/1.911 |
| 3,868,730 | 3/1975 | Kaufer et al. | 3/1.911 |
| 3,958,278 | 5/1976 | Lee et al. | 3/1.911 |
| 4,100,626 | 7/1978 | White | 3/1.91 |

FOREIGN PATENT DOCUMENTS 719308 12/1954 United Kingdom .............. 128/92 CA

OTHER PUBLICATIONS

*Scientific American,* Jan. 1978, excerpt (including outside front cover, pp. 49 and 51).

*Primary Examiner*—Ronald L. Frinks
*Attorney, Agent, or Firm*—Trexler, Wolters, Bushnell & Fosse, Ltd.

[57] ABSTRACT

An interconnection is provided for a human body implant having a polymeric articular surface member supported by a substantially rigid, metallic base plate. Reversely tapered apertures in the supporting base plate enclose portions of the unitary polymeric surface member, which portions protrude past the general interface of the surface member and base plate.

2 Claims, 6 Drawing Figures

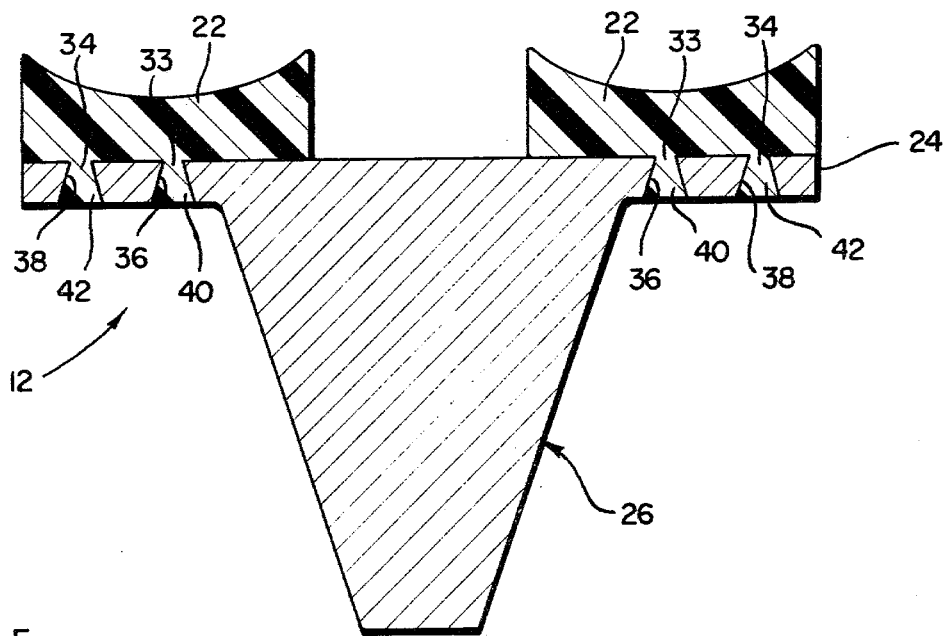
FIG. 4
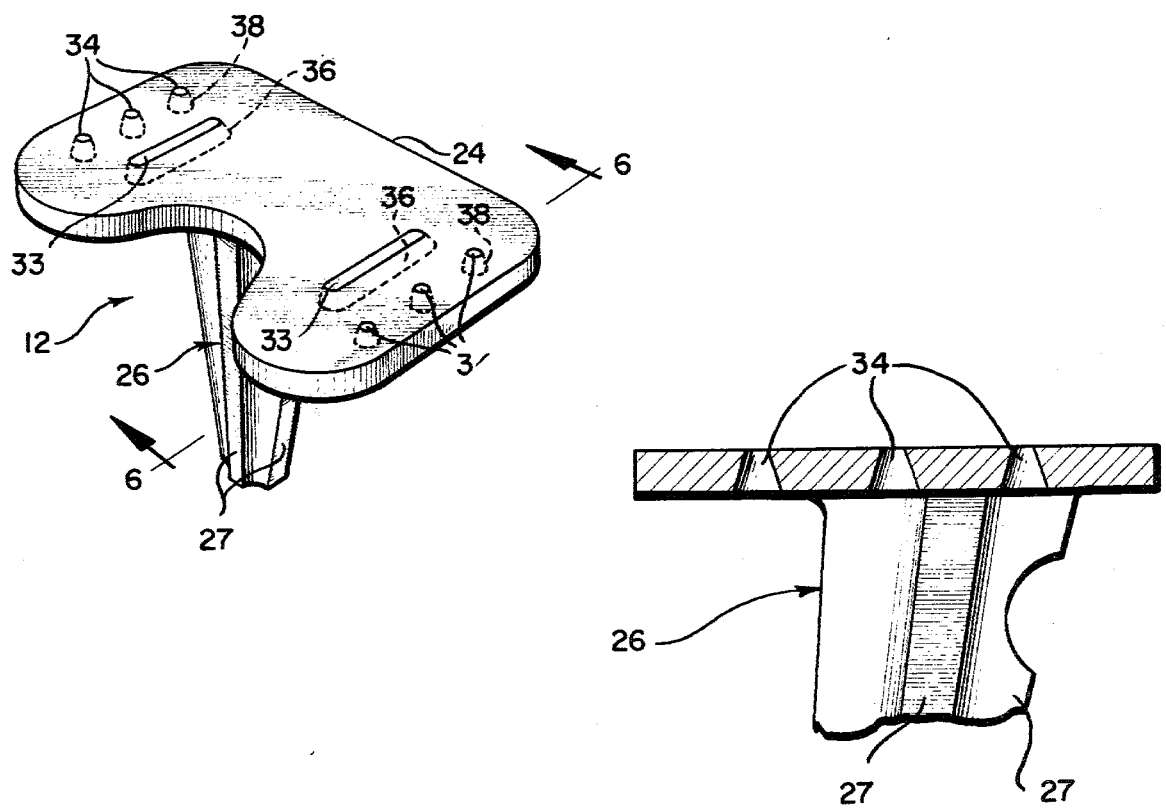
FIG. 5
FIG. 6

METALLO-POLYMERIC PROSTHESIS WITH CAVITIED INTERCONNECTION

BACKGROUND OF THE INVENTION

This invention relates generally to surgical joint prostheses and more specifically to implant devices that are intended to replace and repair load bearing surfaces in articular joints of the human body.

Commercially available knee, hip, and other articular joint prosthesis have become increasingly more successful and popular in recent years. The original metal-to-metal or bone-to-metal designs were improved by Charnley through the development of bearing surfaces combining polished metal and polyethylene of high molecular weight. This combination provided a bearing surface exhibiting low coefficient of friction and a low rate of wear. Charnley also improved the fixation of prosthesis by the use of polymethylmethacrylate cement to fix the components of a prosthesis in the bone.

These developments led, for example, to the knee joint designs of Gunston and Marmor wherein metal runners are cemented to the femur and polyethylene tracks are cemented to the tibia. A patient provided with this type of knee prosthesis essentially has a resurfaced joint with the ultra-high-molecular-weight polyethylene tibial component serving as the load bearing surface. However, the low elastic modulus of ultra-high-molecular-weight polyethylene may, under certain circumstances, permit deformation of the tibial component under load. Due to this deformation, detrimental shear forces are developed between the plastic component and the cement, and this may cause the mechanical bond to weaken.

Thus, schemes for the attachment of a polyethylene articular surface to a metal base plate were developed to improve both the fixation and load distribution of the prosthesis. Such prior methods include the use of a metal retaining wall around the support base with the polymeric articular surface fitted into the retainer by an interference fit or by a locking pin for example. This method is shown in devices known in the art as the Spherocentric knee and the Murray-Shaw knee. In addition, British Pat. No. 719,308 granted to Balog discloses the use of a metal endoskeleton having divergent arms which hold the molded polymeric articular surface in place.

Although generally successful, the methods employed heretofore have not been without their disadvantages. Retaining walls or endoskeletons, in order to provide sufficient lateral resistance to secure the polymeric surface, must be positioned a substantial height above the support plate. This height, in combination with a support plate thickness sufficient to adequately reinforce the articular surfaces, results in a minimum thickness of 8 to 10 mm. for the load bearing portion of the component. Thus, both of these methods are suitable only for thick and relatively deeply concave articular surface designs. In cases where a thin prosthesis is required, due to anatomical or surgical concerns, such methods are unsuitable.

For instance, the strength of an articulating implant and the possibility of future surgical alternatives are dependent largely upon the amount of supporting bone upon which the prosthesis is mounted. Minimum bone removal ensures a stronger cancellous bone structure for firm support and allows a wider choice of surgical alternatives should further modifications become necessary. Any attempt to reduce the thickness of the support or the height of the retaining portions tends to cancel their utility.

It is therefore a general object of the present invention to provide a new and improved articular joint prosthesis.

Another object of the present invention is to provide a thin joint prosthesis having a polymeric articular surface positively secured and supported by a metal base.

Still another object of the present invention is to provide a tibial surface replacement component of minimum profile and having a polymeric articular surface positively secured to a supporting metal plate.

SUMMARY OF THE INVENTION

In the present invention, a thin layer of polymer is secured to a metal base by invasion of the polymer through appropriate perforations in the metal base plate. The base plate is provided with at least one reversely tapered aperture which decreases in cross-section as its directrix approaches the metallo-polymeric interface. The polymeric articular surface is secured on to and through the base by integral union with a polymeric protuberance which fills the aperture and bears against the reversely tapered walls thereof.

BRIEF DESCRIPTION OF THE DRAWINGS

In order that the principles of the present invention may be readily understood, a single embodiment thereof, applied to a knee prosthesis, but to which the application is not to be restricted, is shown in the accompanying drawings wherein:

FIG. 4 is a further enlarged sectional view taken along the line 4—4 of FIG. 3 to show the coherent union of the polymeric and metal components of the tibial prosthesis;

FIG. 5 is an enlarged perspective view of the base plate portion of the tibial prosthesis of FIG. 1;

FIG. 6 is an enlarged sectional view taken along the line 6—6 of FIG. 5.

DETAILED DESCRIPTION OF THE ILLUSTRATED EMBODIMENT

Figure 1:
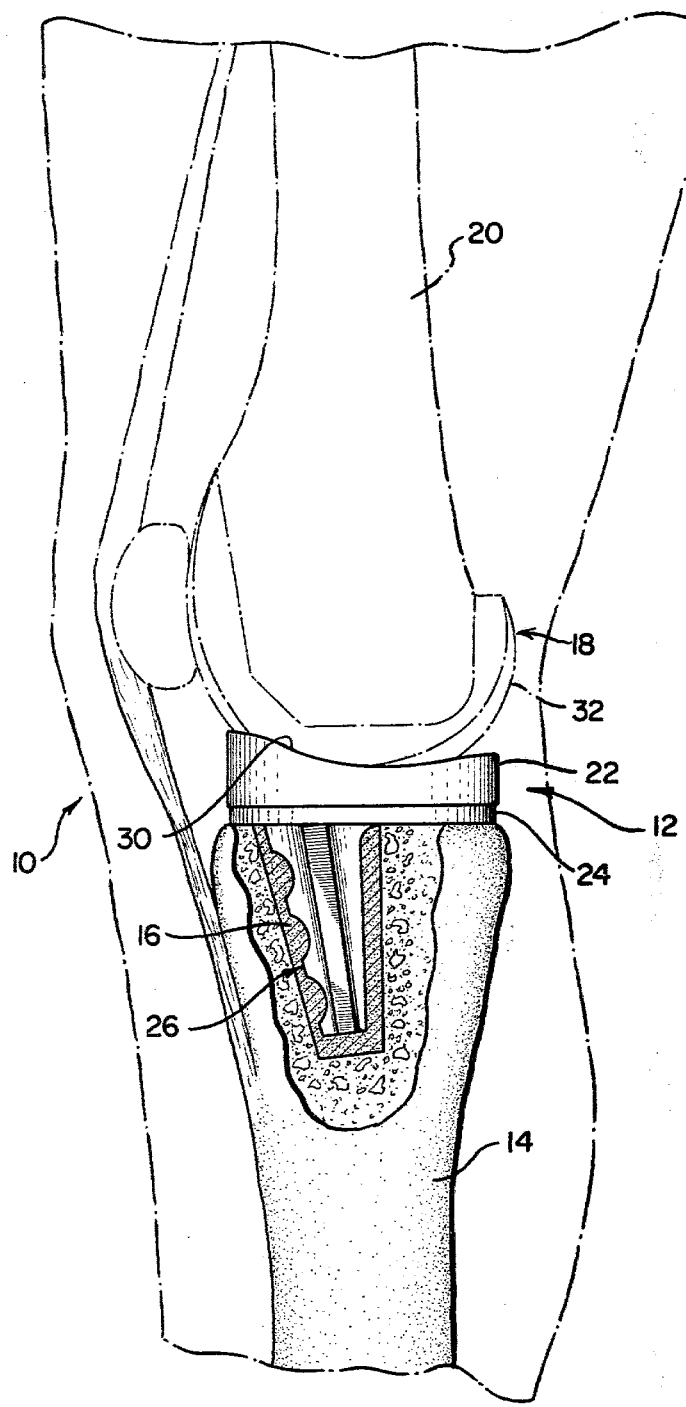
FIG. 1 is a sagittal, partial sectional view representing a human knee implanted with a thin tibial prosthesis constructed in compliance with the present invention.

Referring now in detail to the drawings, specifically to FIG. 1, the knee joint of a human leg is illustrated and there indicated generally by the reference numeral 10. The knee joint 10 is shown to have been repaired by a thin tibial prosthesis 12 that is constructed in compliance with the present invention. Tibial prosthesis 12 is secured at the proximal end of tibia 14, advantageously utilizing fixation by means of suitable quantities of bone cement 16. When installed atop tibia 14, the prosthesis 12 provides a load bearing surface for a femoral component suggested in broken outline at 18 installed at the distal end of femur 20.

Repair of the knee 10 will have been medically indicated by some substantial degree of disfunction resulting from injury or disease. In the initial stages of surgery, certain structures of the knee joint will be removed selectively in order to install the tibial prosthesis 12 and the companion femoral prosthesis 18.

In FIG. 1, the tibial prosthesis 12 is seen to comprise a thin articulating surface member 22 suitably fabricated from an anti-friction polymer such as high molecular weight polyethylene. Articular surface member 22 is supported by a base plate 24 advantageously made of metal compatible with the human body such as a cobalt-chromium-molybdenum alloy.

In order to promote secure fixation of prosthesis 12 in the bony head of tibia 14, the metallic base plate 24 is formed with a pendant connecting stem 26 for extending downwardly into an excavated cavity in the tibia, stem 26 including radiant fins 27, the anterior of which is scalloped or relieved for interlocking with the cement 16.

Figure 2:
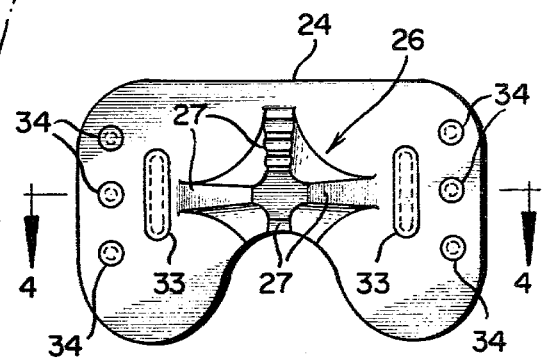
FIG. 2 is an enlarged bottom plan view of the tibial prosthesis of FIG. 1, illustrating the reverse tapered apertures therein and the fixation structures used in mounting the prosthesis in place at the proximal end of the tibia.

FIG. 2 shows that the connecting stem 26 is located centrally beneath base plate 24. However, an intercondylar web 29 may be omitted; and paired connecting stems may then be disposed in outboard position to allow retention of the cruciate ligaments, or other desired medical objectives.

Figure 3:
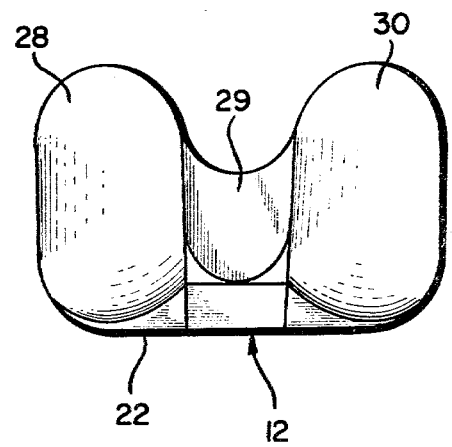
FIG. 3 is a top plan view of the tibial prosthesis of FIG. 2.

Turning to FIG. 3 for further description of the tibial prosthesis 12, polymeric articular surface member 22 is seen to comprise a pair of concave articular surface defining elements 28 and 30, adapted to matably receive cooperating condylar portions 32 of femoral prosthesis 18 as is shown in FIG. 1.

Returning to FIG. 2, base plate 24 includes channeled apertures 33 and circular apertures 34. According to the features of the present invention and as is shown in FIGS. 4, 5, and 6, the apertures and 33 and 34 are defined respectively by reversely tapering walls 36 and 38 of substantially frusto-conical cross-section in order to achieve secure connection of base plate 24 and polymeric articular surface member 22 using the interlocking of integral keying portions 40 and 42 with the tapering walls 36 and 38. The walls 36 and 38 are defined by a triangular generatrix which increases in width as the directrix recedes from the interface of member 22 and base plate 24.

The advantageous geometry of apertures 33 and 34 allows an interconnection of articular surface member 22 and base plate 24 which is highly resistant to both shear forces and longitudinal displacement forces acting on articular surface member 22.

Since this interconnection is accomplished by the protrusion of integral portions of articular surface member 22 into base plate 24, surface member 22 need only be thick enough to provide a bearing surface as it need not receive metallic protrusions which would otherwise substantially increase the overall height of the tibial prosthesis 12.

The drawings and the foregoing descriptions are not intended to represent the only form of the invention in regard to the details of its construction and manner of use. Changes in form and in the proportion of parts as well as the substitution of equivalents, are contemplated as circumstances may suggest or render expedient; and although specific terms have been employed, they are intended in the generic and descriptive sense only and not for purposes of limitation, the scope of the invention being delineated in the following claims:

The invention is claimed as follows:

1. A metallo-polymeric human body implant with cavitied interconnection, said implant comprising: a substantially rigid, metallic support member including means for skeletal fixation; an articular surface member of polymeric, anti-friction bearing material having a first surface for articular contact with a cooperating joint element and a second surface disposed in matable contact with said support member axially opposite said skeletal fixation means; and means interconnecting said support member and said articular surface member, including aperture means in said support member having tapered walls diverging away from said second surface, said interconnecting means further including polymeric keying means integral and confluent with said articular surface member and tightly matably engaging the tapered walls of said aperture means, said keying means stopping adjacent the wider end of said tapered walls whereby to provide secure bone-to-metal contact about said skeletal fixation means.

2. A human body implant according to claim 1 wherein said aperture means comprises a plurality of frusto-conical apertures.

* * * * *